(12) United States Patent
Junge et al.

(10) Patent No.: US 7,580,758 B2
(45) Date of Patent: Aug. 25, 2009

(54) IMPLANTABLE ELECTRODE DEVICE

(75) Inventors: Agur Junge, Berlin (DE); Gernot Kolberg, Berlin (DE); Hans-Gerd Staeger, Sprockoevel (DE)

(73) Assignee: Biotronik CRM Patent AG (CH)

( * ) Notice: Subject to any disclaimer, the term of this patent is extended or adjusted under 35 U.S.C. 154(b) by 465 days.

(21) Appl. No.: 11/461,596

(22) Filed: Aug. 1, 2006

(65) Prior Publication Data
US 2007/0043415 A1 Feb. 22, 2007

(30) Foreign Application Priority Data
Aug. 18, 2005 (DE) .................. 10 2005 039 040

(51) Int. Cl.
A61N 1/05 (2006.01)
(52) U.S. Cl. ............................................. 607/127
(58) Field of Classification Search ............... 607/127
See application file for complete search history.

(56) References Cited

U.S. PATENT DOCUMENTS

| 4,106,512 | A | | 8/1978 | Bisping |
| 5,354,327 | A | * | 10/1994 | Smits ................. 607/116 |
| 5,514,173 | A | | 5/1996 | Rebell et al. |
| 5,716,390 | A | * | 2/1998 | Li ...................... 607/127 |
| 5,837,006 | A | * | 11/1998 | Ocel et al. ............. 607/127 |
| 6,704,605 | B2 | | 3/2004 | Soltis et al. |
| 6,813,521 | B2 | | 11/2004 | Bischoff et al. |
| 6,819,959 | B1 | * | 11/2004 | Doan et al. ............. 607/127 |
| 6,931,285 | B2 | | 8/2005 | Bischoff |
| 2002/0188338 | A1 | | 12/2002 | Bischoff |
| 2002/0188340 | A1 | | 12/2002 | Bischoff et al. |
| 2002/0193860 | A1 | | 12/2002 | Bischoff et al. |
| 2003/0144722 | A1 | | 7/2003 | Soltis et al. |

FOREIGN PATENT DOCUMENTS
DE 37 12 082 A1 10/1988
EP 00 15 229 B1 9/1980

OTHER PUBLICATIONS
German Search Report, issue by the German Patent Office on May 3, 2006, for patent application serial No. DE 10 2005 039 040.4.

* cited by examiner

Primary Examiner—Carl H Layno
Assistant Examiner—Jeremiah T Kimball
(74) Attorney, Agent, or Firm—Craig A. Fieschko, Esq.; DeWitt Ross & Stevens S.C.

(57) ABSTRACT

An implantable electrode device, particularly a cardiological electrode device, comprises an oblong, hose-like electrode body and a helical screw-in electrode, which is displaceable on the distal end of the electrode body between a retracted passive position inside the electrode body and an extended, active fixing position outside the electrode body, which is displaceable by a rotational movement of its electrode line, with the aid of a spindle-type cam controller, between the retracted passive position and the extended fixing position. The cam controller is formed by a separate cam coil, which is fixedly mounted in the electrode body and coaxially to the electrode supply line and, in addition, by a cam body, which is mounted on the electrode supply line rotationally fixed thereto and engages in the cam coil.

20 Claims, 4 Drawing Sheets

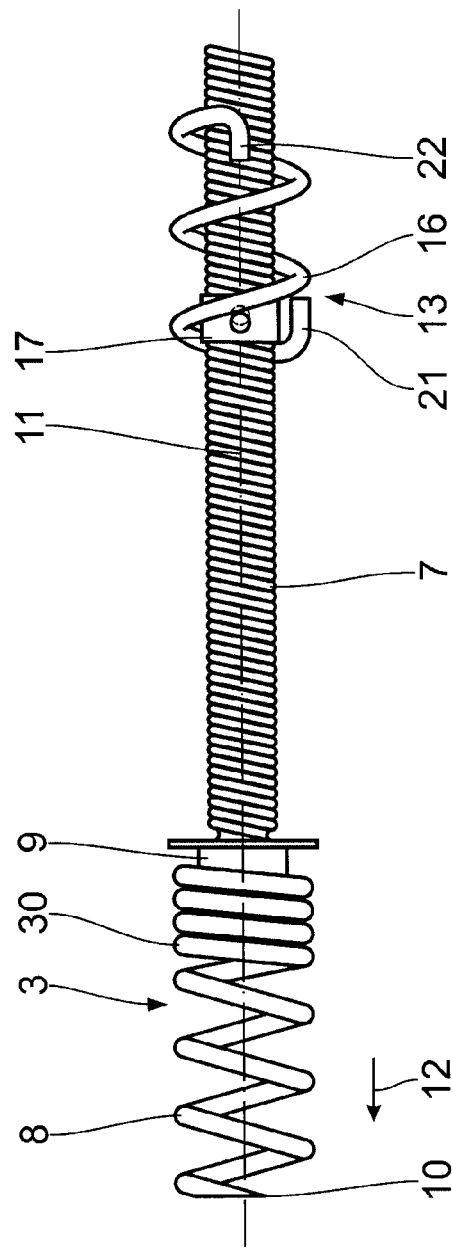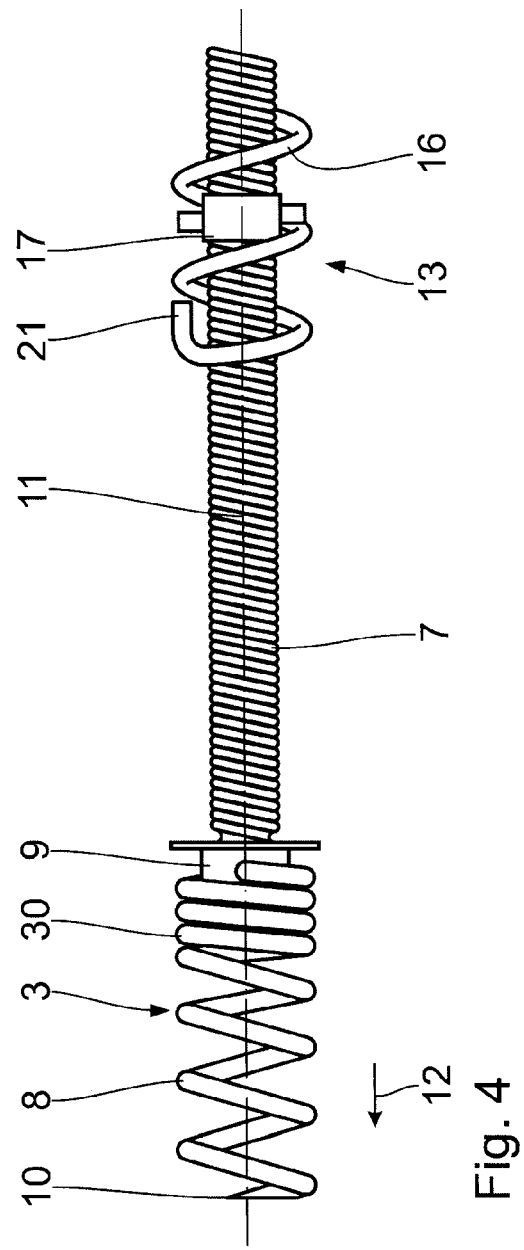

IMPLANTABLE ELECTRODE DEVICE

FIELD OF THE INVENTION

The present invention relates to an implantable electrode device and particularly a cardiological electrode device.

BACKGROUND OF THE INVENTION

Electrode systems are known from various publications, such as US 2002/0188338 A1, US 2002/0188340 A1, or US 2002/0193860 A1.

These known devices have an oblong, hose-like electrode body, on whose distal end a helical screw-in electrode is displaceable between a retracted passive position inside the electrode body and an extended active fixing position. The purpose of this screw-in electrode seated on the tip of the electrode device is its stable and permanent anchoring in cardiological tissue suitable for the particular diagnosis and treatment. In order to ensure this, the helical screw-in electrode is screwed into the tissue like a corkscrew, which is implemented through a rotational movement of the electrode supply line powering the screw-in electrode during extension of the screw-in electrode from the retracted passive position into the extended fixing position.

The conversion of the rotational movement of the electrode supply line into an additional translational movement of the screw-in electrode for extension into the fixing position is caused with the aid of a spindle-type cam controller. In the electrode devices according to the above-mentioned publications, a cam projection situated on the electrode body engages directly in the coil of the screw-in electrode for this purpose. Because of the positioning of the cam, the electrode body on the distal end of the electrode device on which it is mounted must be designed as relatively rigid and stable. This prevents a more flexible design of the distal end, which is viewed as advantageous in modern implantable electrode devices in regard to an implantation procedure with as little irritation as possible.

In this context, a certain spatial separation between the cam controller for the translational movement of the screw-in electrode and the electrode itself is known from US 2003/0144722 A1. The screw-in electrode is situated having its proximal end on a bearing body therein, which is guided displaceably like a spindle using an external thread in a corresponding internal thread in the electrode body. However, a separate stylet must be inserted through the electrode body and coupled rotatably to the bearing body for the rotational drive of the bearing body.

SUMMARY OF THE INVENTION

The present invention is based on the object of improving the cam controller for extending and retracting the screw-in electrode in such a way that in spite of a simple and cost-effective basic construction, the distal end of the electrode body having the screw-in electrode is designed more flexibly and secure actuation of the screw-in electrode is made possible.

This object may be achieved by decoupling of the helix forming the screw-in electrode from the cam controller which causes its extension and retraction movement, and providing a separate cam coil in the electrode body for this purpose. A cam body on the electrode supply line, which is mounted rotationally fixed in relation thereto, may engage in this cam coil.

Notwithstanding the fact of whether the cam body is implemented as a closed cam ring having at least one cam projection engaging in the cam coil, or as an open helix ring having a slope corresponding to the cam coil, the present invention still allows the attachment of the cam body on the part of the electrode supply line implemented as the conduction coil. A conduction coil of this type is flexible and may be coupled with only a short transition to the coil of the screw-in electrode. A high flexibility of the electrode device in the area of the distal end may thus be achieved.

In each case, the claimed closed cam ring or open helix ring is preferably a constructively simple, preferably one-piece, and easily mountable part precisely like the cam coil cooperating therewith, which is preferably a wire part which is correspondingly formed and bended.

To protect the screw-in electrode and the electrode supply line connected thereto against "overrotation" both during retraction and also extension, according to a further preferred embodiment, rotation stops are provided, which delimit the rotational movement of the electrode supply line. These rotation stops may be formed by projections on the electrode body projecting into the movement path of the cam body or—even more simply—by the ends of the wire-shaped cam coil bent into the movement path of the cam body.

Depending on the intended use of the electrode device according to the present invention, its distal end may be configured in different embodiments in regard to the housing of the cam controller. Thus, a space-saving housing may be provided in an insulated housing radially inside an annular electrode situated in front of the distal electrode end. The cam controller may also be situated in a separate head housing closely assigned to the bearing of the screw-in electrode. More preferably, this head housing may receive a bearing shaft supporting the screw-in electrode, on which the cam body may be positioned in turn.

According to further preferred embodiments of the present invention, the cross-section of the screw-in electrode may be implemented as non-round, particularly ellipsoidal or rectangular, for example, the cross-sectional dimension running radially to the screw axis being larger than that running parallel thereto. The effect is thus achieved that at lower displacement volumes in the axial direction, larger forces may be absorbed. The screw-in electrode may thus be screwed in using less torque and higher retaining forces may be achieved. The foregoing configuration of the screw-in coil may also be advantageously implemented separately from the features noted above.

In summary, the present invention, with its preferred embodiments, forms a basis for numerous advantages, such as a simple, cost-effective construction due to a low piece count and simple materials, low pole spacing from the screw-in electrode to the following annular electrode (can be less than 10 mm), protection of the screw-in electrode from damage due to overrotation, broadband adaptability, e.g., to implement DEFI electrode devices, a highly flexible head construction, and allowing "mapping" to be able to be performed with the aid of the screw-in electrode.

Further features, advantages, and details of the present invention may be inferred from the following description, in which exemplary embodiments of the subject matter of the present invention are explained in greater detail on the basis of the attached drawing.

BRIEF DESCRIPTION OF THE DRAWINGS

FIGS. 3 and 4 show detail views of the cam controller having the screw-in electrode in the fixing positioned and passive position, respectively.

DETAILED DESCRIPTION OF PREFERRED VERSIONS OF THE INVENTION

Figure 1:
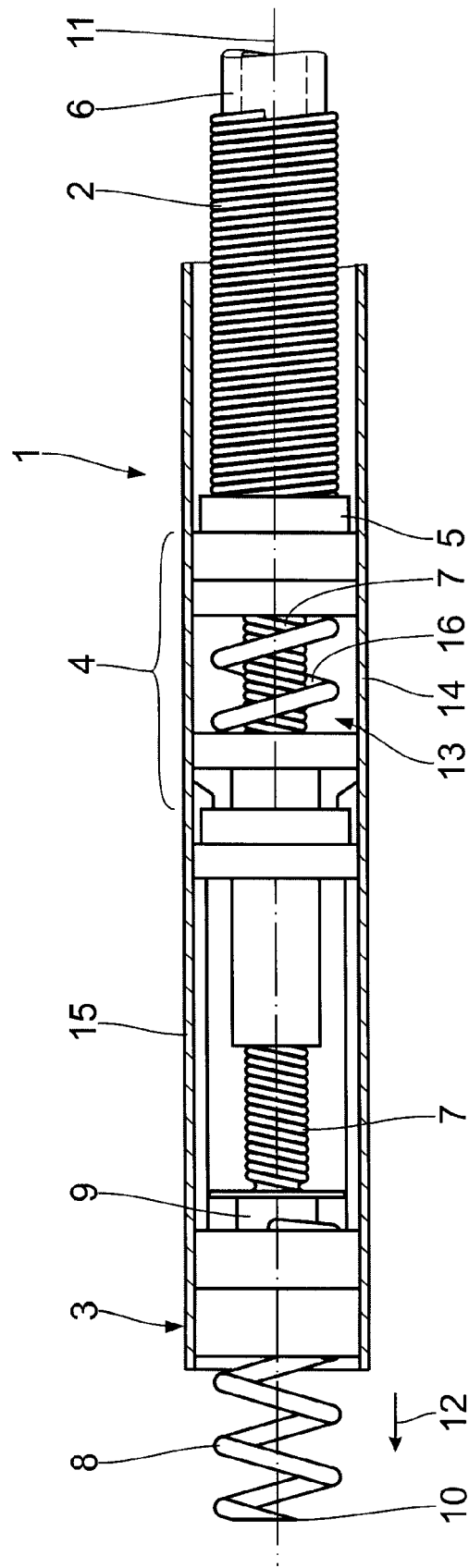
FIG. 1 shows a schematic side view of the distal end of an electrode device having a screw-in electrode and its cam controller.

As shown in FIG. 1, a cardiological electrode device has an oblong, hose-like electrode body 1, which is manufactured from a flexible silicone material, for example. In the lumen of this electrode body 1 (not shown in greater detail) a first conduction coil 2 of large diameter is guided, which is connected electrically to an annular electrode 4 situated in front of the distal end 3 of the electrode device via a contact sleeve 5. An insulating hose 6 is guided inside the external conduction coil 2, in which a further conduction coil 7 of smaller diameter runs in turn for contacting the screw-in electrode 8 situated at the distal end 3. This conduction coil 7 is manufactured like a coiled spring coiled on a block from a flexible metal material and ends in the area of the distal end 3 in a bearing body 9 for the screw-in electrode 8. The latter is implemented as a helical wire coil having a tip 10 and, for placement at a suitable point in the ventricle of the heart of an electrode receiver, for example, is screwed into the cardiac tissue like a corkscrew through a rotational movement around the axis of rotation 11 and a translational extension movement as shown by arrow 12.

Figure 2:
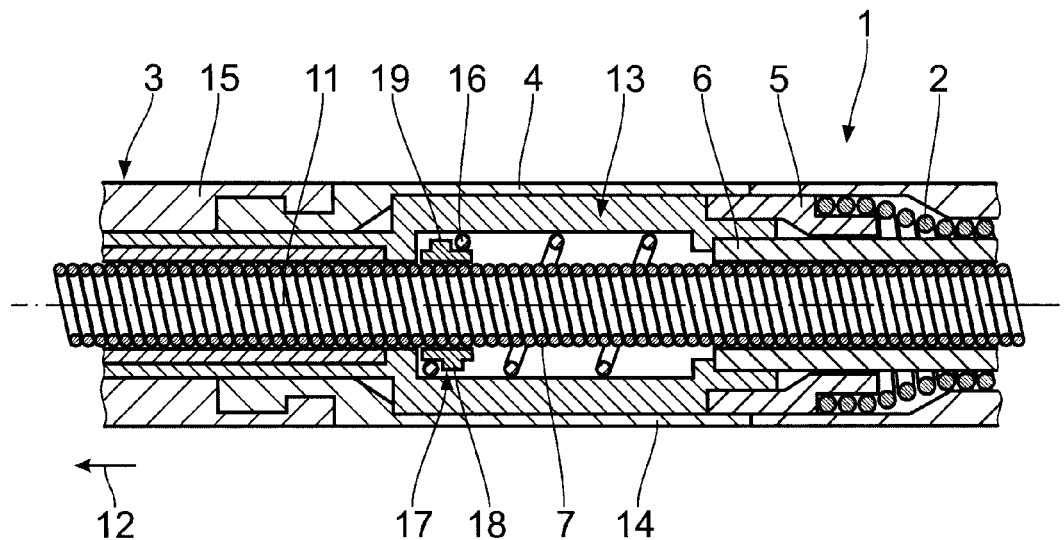
FIG. 2 shows an axial section of the cam controller for the screw-in electrode in a first embodiment.

The rotational movement around the axis of rotation 11 is caused by a corresponding rotation of the conduction coil 7 around its own axis from the proximal end of the electrode device (not shown). The extension movement 12 and opposite retraction movement are also derived from this rotational movement with the aid of a cam controller identified as a whole by 13, which is housed in the exemplary embodiment shown in FIGS. 1 and 2 radially inside the annular electrode 4. For this purpose, the latter is provided on its interior with an insulating housing 14 made of insulating material—e.g., silicone—which continues in the direction of the distal end 3 in a tubular shape in an external insulation 15 of the electrode body 1 adjoining the annular electrode 4.

Figure 5:
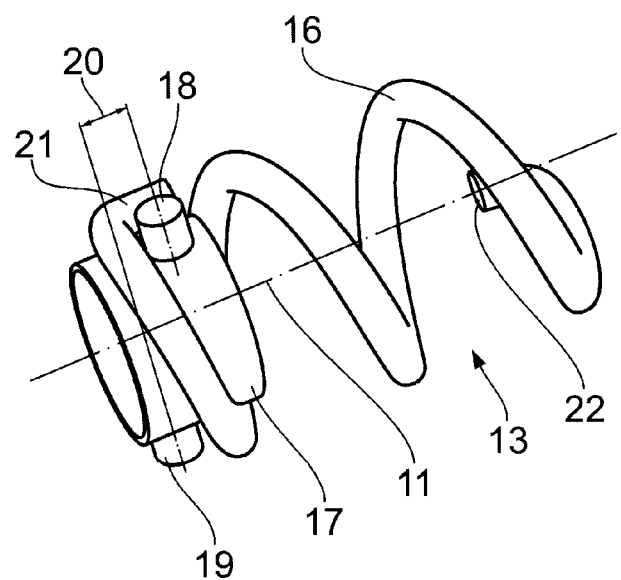
FIG. 5 shows an enlarged perspective illustration of a cam coil having a cam body engaging therein.

As shown in FIGS. 2 through 5, a cam coil 16, which comprises an open-coiled, rigid wire, is situated rotationally fixed in the insulating housing 14. The open internal diameter of the cam coil 16 is significantly larger than the external diameter of the conduction coil 7. A closed cam ring 17, which has two diametrically opposite, radially projecting cam projections 18, 19, is seated rotationally fixed thereon in the area of the cam controller 13. These cam projections have a small offset 20 in the axial direction (FIG. 5). The external diameter of the cam ring 17 is somewhat smaller than the internal diameter of the cam coil 16, so that the ring may move through the cam coil 16 in the axial direction, the cam projections 18, 19 engaging in the cam coil—as shown in FIGS. 3 through 5. The cam ring 17, which is manufactured in one piece, is made of a metal material and may be welded onto the conduction coil 7, for example.

During a rotational movement of the conduction coil 7, the cam ring 17 is moved translationally in the axial direction by the engagement of the cam projections 18, 19 in the cam coil 16, so that the screw-in electrode 8 coupled to the conduction coil 7 via the bearing body 9 also experiences, in addition to the rotational movement, the translational movement in the extension direction 12 and opposite thereto—depending on the rotational direction of the conduction coil 7.

As is shown in FIGS. 3 through 5, the ends 21, 22 of the cam coil 16 are bent inward parallel to the axis of rotation 11, so that they engage in the movement path of the cam projections 18, 19 and are thus used as rotation stops for delimiting the rotation of the conduction coil 7 and thus the retraction and extension movements of the screw-in electrode 8.

On the basis of the arrangements of the cam controller 13 below the annular electrode 4 shown in FIGS. 1 through 5, the area between this and the distal end 3 in the area of the external insulation 15 may be kept flexible, through which the electrode device may be implemented in a "soft tip embodiment".

Figure 6:
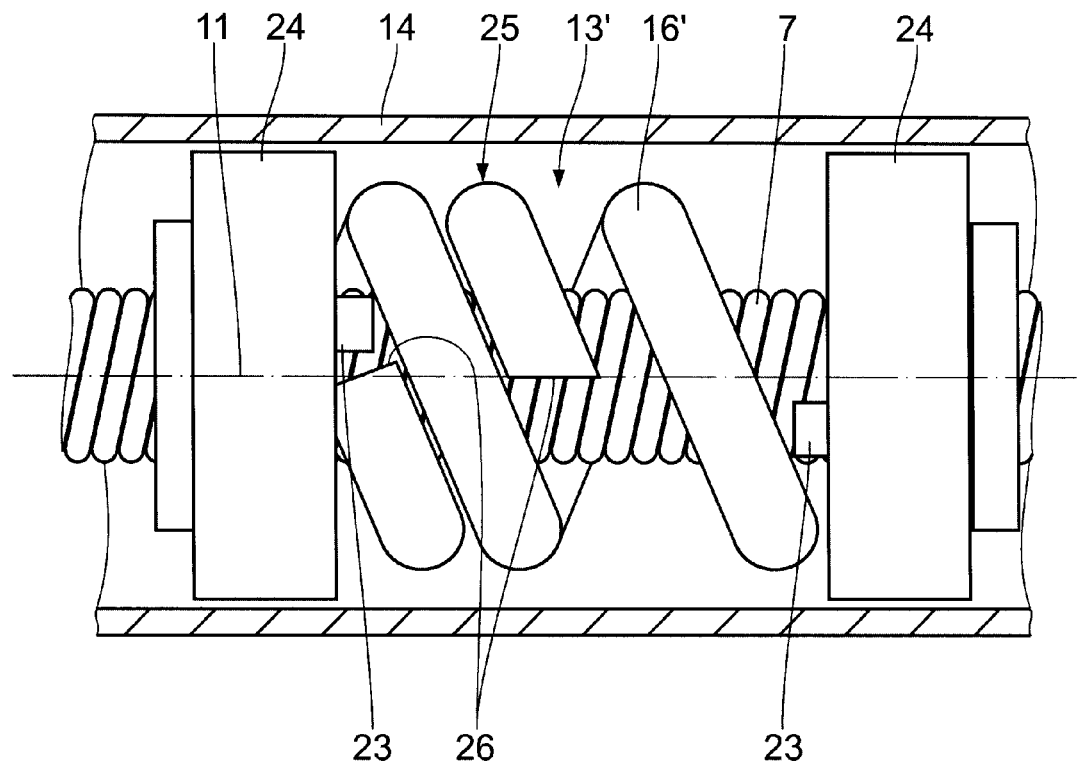
FIG. 6 shows a detail side view of a cam controller in a second embodiment.

In the embodiment of the cam controller 13' shown in FIG. 6, a wire cam coil 16' is again provided, this having no bent-in ends 21,22, however. Rather, projections 23, each engaging axially in the area of the cam coil 16', are formed as rotational stops for delimiting the rotational movement of the conduction coil 7, which project in the axial direction from fixed bearing rings 24 flanking the cam controller 13'. Furthermore, in this embodiment, an open helix ring 25 is provided as a cam body, which is open-coiled analogously to the cam coil 16' and has a corresponding slope. The helix ring 25, which is connected rotationally fixed to the conduction coil 7, runs coaxially-translationally in the cam coil 16' during a rotation of the conduction coil 7, so that the conduction coil 7 is displaced in the extension direction 12 or opposite thereto—depending on the rotational direction of the conduction coil 7—to retract and extend the screw-in electrode 8. The open front faces 26 of the helix ring 25 each stop at the end of the corresponding advancing movements on the projections 23 of the bearing rings 24 to delimit the rotational and translational movement of the conduction coil 7 and thus the screw-in electrode 8.

Figure 7:
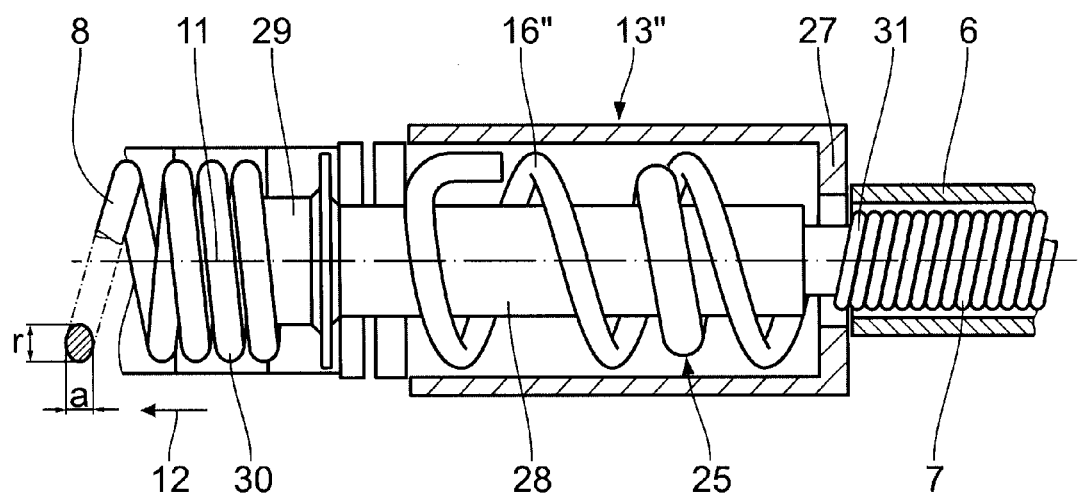
FIG. 7 shows a partially cutaway side view of the distal end of an electrode device in a second embodiment.

In the embodiment shown in FIG. 7, the cam controller 13'' is shifted directly in front of the distal end 3 of the electrode device and is housed in a separate head housing 27. This is also used as a mounting for a bearing 28, which is connected rotationally fixed to the conduction coil 7. This bearing shaft 28 penetrates the cam coil 16' positioned rotationally fixed in the has housing 27 and, corresponding to the embodiment shown FIG. 6, carries a helix ring 25, which engages with the cam coil 16''. In the direction toward the distal end 3, the bearing shaft 28 is provided with the bearing head 29 on which the screw-in electrode 8—not shown as such—is attached and electrically contacted with the aid of tightly coiled fixing windings 30. Upon a rotation of the conduction coil 7, the bearing shaft 28 is also rotated and moves translationally in the extension direction 12, so that the screw-in electrode 8 may be extended from the electrode body 1 while rotating and screwed into appropriate tissue. The contacting of the screw-in electrode 8 is performed via a direct electrical connection between the windings 30, the bearing shaft 28, and the conduction coil 7.

As is also indicated in FIG. 7, the cross-section of the wire material of the screw-in electrode 8 is implemented as elliptical, the cross-sectional direction r running radially to the screw axis 11 being greater than the cross-sectional dimension a running parallel thereto.

The invention is not intended to be limited to the preferred versions of the invention described above, but rather is intended to be limited only by the claims set out below. Thus, the invention encompasses all different versions that fall literally or equivalently within the scope of these claims. Any reference numerals present in the claims merely refer the reader to the preferred versions of the invention shown in the drawings to enhance the reader's understanding, and do not limit the claims to the preferred versions shown in the drawings.

What is claimed is:

1. An implantable cardiological electrode device, comprising
   a. an elongated tubular electrode body,
   b. an electrode supply line extending within the electrode body,
   c. a helical screw-in electrode displaceable at the distal end of the electrode body between a retracted passive position inside the electrode body and an extended active fixing position outside the electrode body,
   d. a cam controller including:
      (1) a cam coil fixed in the electrode body and coaxially with the electrode supply line,
      (2) a cam body fixed on the electrode supply line and engaging the cam coil, and
      (3) rotational stops which interact with the cam body to delimit the rotational movement of the electrode supply line, the rotational stops being defined by opposing ends of the cam coil bent into the path of movement of the cam body,
   wherein relative rotation between the electrode supply line and the electrode body engages the cam body with the cam coil to displace the electrode between the retracted passive position and the extended active fixing position.

2. The electrode device of claim 1 wherein the cam body is defined by an open helix ring about the electrode supply line, the cam body having a rotational pitch corresponding to the rotational pitch of the cam coil.

3. The electrode device of claim 1 wherein the cam controller is situated within an insulated housing radially inside an annular electrode situated in front of the distal electrode end.

4. The electrode device of claim 1 wherein the cam body is situated on a conduction coil section of the electrode supply line, wherein:
   a. the cam body surrounds the conduction coil section of the electrode supply line, and
   b. at least the portion of the electrode supply line within the cam body is defined by a coil.

5. The electrode device of claim 1 wherein the cam body is situated on a bearing shaft which supports the screw-in electrode, and which mechanically and electrically connects the distal end of a conduction coil section of the electrode supply line to the screw-in electrode.

6. The electrode device of claim 1 wherein the screw-in electrode is made of a wire material having a nonround wire cross-section, the cross-sectional dimension (r) running radially to the screw axis being greater than the cross-sectional dimension (a) directed parallel thereto.

7. The electrode device of claim 6 wherein the wire cross-section is shaped as elliptical or rectangular.

8. The electrode device of claim 1 wherein the cam coil has a pitch sized with respect to the cam body such that the cam body may translate between adjacent loops of the cam coil without engaging the cam coil.

9. The electrode device of claim 1 wherein the cam body:
   a. is situated at least partially within the inner circumference of the cam coil, and
   b. has projections extending radially outwardly therefrom to rest between adjacent loops of the cam coil.

10. An implantable electrode device comprising:
    a. an elongated tubular electrode body,
    b. an electrode supply line rotatably and translatably situated within the electrode body, the electrode supply line being conductively connected to a helical screw-in electrode,
    c. a cam controller including:
       (1) a helical cam coil formed of a series of loops extending about the electrode supply line, and
       (2) a cam body rotatably and translatably engaged to the cam coil,
    wherein:
    i. the electrode body is fixed to one of the cam coil and the cam body, and the electrode supply line is fixed to the other of the cam coil and the cam body, such that relative rotation between the electrode body and the electrode supply line translates the electrode body with respect to the electrode supply line, and
    ii. wherein the cam coil has a pitch sized with respect to the cam body such that the cam body may translate between adjacent loops of the cam coil without engaging the cam coil.

11. The electrode device of claim 10 wherein:
    a. the cam coil is fixed with respect to the electrode body, and
    b. the cam body is fixed with respect to the electrode supply line.

12. The electrode device of claim 10 wherein:
    a. the cam coil extends helically between bent ends, and
    b. the cam body has a portion within the inner circumference of the helix of the cam coil, and projections extending therefrom, wherein the projections interfere with the bent ends to serve as rotational/translational stops for the cam body within the cam coil.

13. The electrode device of claim 10 wherein:
    a. the cam coil is fixed with respect to the electrode body, and
    b. the cam body is defined by a helical ring extending about and engaged to the electrode supply line, wherein the cam body is helically intermeshed with the cam coil.

14. The electrode device of claim 13 wherein the cam coil is situated between stops, wherein the stops bear projections limiting the rotation of the cam body.

15. The electrode device of claim 10 wherein the cam body is defined by a helical section intermeshed with the cam coil.

16. An implantable electrode device comprising:
    a. an elongated tubular electrode body,
    b. an electrode supply line rotatably and translatably situated within the electrode body, the electrode supply line being conductively connected to a helical screw-in electrode,
    c. a cam controller including:
       (1) a wire cam coil formed of a series of loops, the cam coil having an inner diameter, and an opposing outer diameter spaced radially inwardly from, and fixed with respect to, the electrode body, and
       (2) a cam body fixed with respect to the electrode supply line rotatably and translatably engaged to the cam coil, the cam body being situated at least partially within the inner circumference of the cam coil, and having projections extending radially outwardly therefrom, the projections being situated between adjacent loops of the cam coil, whereby relative rotation between the electrode body and the electrode supply line translates the electrode body with respect to the electrode supply line.

17. The electrode device of claim 16 wherein:
 a. the cam coil extends helically between bent ends, and
 b. the cam body has a portion within the inner diameter of the cam coil, and projections extending radially outwardly therefrom.

18. The electrode device of claim 16 wherein the cam coil has a pitch such that each projection can only contact one of the loops of the cam coil at a time.

19. The electrode device of claim 16 wherein the cam coil has opposing ends which are bent to obstruct the rotation and/or translation of the cam body past the ends.

20. The electrode device of claim 16 wherein the cam coil has a pitch sized with respect to the cam body such that the cam body may translate between adjacent loops of the cam coil without engaging the cam coil.

* * * * *